United States Patent
Imanishi et al.

(10) Patent No.: US 12,014,499 B2
(45) Date of Patent: Jun. 18, 2024

(54) BIOIMAGE ACQUIRING DEVICE, CONVERTER GENERATING DEVICE, BIOIMAGE GENERATING METHOD, CONVERTER GENERATING METHOD, AND RECORDING MEDIUM

(71) Applicant: E-GROWTH CO., LTD., Kyoto (JP)

(72) Inventors: Keiho Imanishi, Kyoto (JP); Megumi Nakao, Kyoto (JP)

(73) Assignee: E-GROWTH CO., LTD., Kyoto (JP)

( * ) Notice: Subject to any disclaimer, the term of this patent is extended or adjusted under 35 U.S.C. 154(b) by 431 days.

(21) Appl. No.: 17/615,454

(22) PCT Filed: Jul. 2, 2020

(86) PCT No.: PCT/JP2020/026008
§ 371 (c)(1),
(2) Date: Nov. 30, 2021

(87) PCT Pub. No.: WO2021/006174
PCT Pub. Date: Jan. 14, 2021

(65) Prior Publication Data
US 2022/0230308 A1 Jul. 21, 2022

(30) Foreign Application Priority Data
Jul. 5, 2019 (JP) .................................. 2019-126430

(51) Int. Cl.
*G06T 7/00* (2017.01)
*A61B 5/055* (2006.01)
(Continued)

(52) U.S. Cl.
CPC ............ *G06T 7/0012* (2013.01); *A61B 5/055* (2013.01); *A61B 6/03* (2013.01); *G01T 1/161* (2013.01)

(58) Field of Classification Search
CPC ......... G06T 7/0012; A61B 5/055; A61B 6/03; G01T 1/161
(Continued)

(56) References Cited

U.S. PATENT DOCUMENTS

| | | | |
|---|---|---|---|
| 2019/0128989 A1 | 5/2019 | Braun et al. | |
| 2021/0010953 A1* | 1/2021 | Adler | G06F 18/24 |
| 2021/0272277 A1* | 9/2021 | Ogino | G06N 3/045 |

FOREIGN PATENT DOCUMENTS

JP 2004061500 A * 2/2004 ........... G06T 7/0004

OTHER PUBLICATIONS

Kenji Ino, "An approach to metal artifacts in CT scan" [online], [Jun. 21, 2019 search], Internet [URL:https://www.innervision.co.jp/sp/ad/suite/canonmedical/sup201512/session1-1] (Japanese ver. and English ver.).

(Continued)

*Primary Examiner* — Gabriel I Garcia
(74) *Attorney, Agent, or Firm* — Rimon P.C.

(57) ABSTRACT

A bioimage acquiring device includes a first conversion unit that performs a first conversion process wherein a negative bioimage is converted using a first converter so as to acquire a converted bioimage which is the result of the conversion, and a classifying unit that performs a first classifying process wherein a determination is made as to whether the converted bioimage is a positive bioimage or a negative bioimage, using a classifier for determining whether an image is a negative bioimage or a positive bioimage, wherein the first conversion unit performs a learning process using the determination result obtained by the classifying unit and the converted bioimage, performs an update process for updating the first converter, and receives a new negative bioimage, and the first conversion unit converts the new negative bioimage using the updated first converter to (Continued)

acquire a converted bioimage which is the result of the conversion.

14 Claims, 15 Drawing Sheets

(51) Int. Cl.
*A61B 6/03* (2006.01)
*G01T 1/161* (2006.01)

(58) Field of Classification Search
USPC .......................................................... 382/128
See application file for complete search history.

(56) References Cited

OTHER PUBLICATIONS

Yanbo Zhang, Hengyong Yu, "Convolutional Neural Network Based Metal Artifact Reduction in X-ray Computed Tomography" [Online], [Jul. 3, 2019 search], Internet [URL: https://arxiv.org/abs/1709.01581].

Zhao, Shuyang et al., Removing Ring Artifacts in CBCT Images Via Generative Adversarial Network, 2018 IEEE International Conference on Acoustics, Speech and Signal Processing, Sep. 13, 2018, p. 1055-1059 "2. The Proposed Method".

International Search Report issued in International Patent Application No. PCT/JP2020/026008, dated Sep. 15, 2020; with English translation.

\* cited by examiner

BIOIMAGE ACQUIRING DEVICE, CONVERTER GENERATING DEVICE, BIOIMAGE GENERATING METHOD, CONVERTER GENERATING METHOD, AND RECORDING MEDIUM

CROSS-REFERENCE OF RELATED APPLICATIONS

This application is the U.S. National Phase under 35 U.S.C. § 371 of International Patent Application No. PCT/JP2020/026008, filed on Jul. 2, 2020, which in turn claims the benefit of Japanese Application No. 2019-126430, filed on Jul. 5, 2019, the entire disclosures of which Applications are incorporated by reference herein.

FIELD OF THE INVENTION

The present invention relates to a bioimage acquiring device that acquires a positive bioimage, which is a bioimage with few defects, from a negative bioimage, which is a bioimage with defects such as metal artifacts.

BACKGROUND ART

In X-ray CT, if the imaged object contains a high absorber of X-rays (for example, metal), precise calculation of CT values is hindered, and as a result, an artifact that has a large detrimental effect is produced.

For this problem, there is an algorithm called the Metal Artifact Reduction (MAR) algorithm that corrects metal artifacts (see Non-Patent Document 1).

There are also other techniques for reducing artifacts using deep learning (see Non-Patent Document 2).

PRIOR ART DOCUMENTS

Non-Patent Documents

Non-patent document 1: Kenji Ino, "Approach to metal artifacts in CT scans," [online], [retrieved on Jun. 21, 2019], Internet: [URL: https://www.innervision.co.jp/sp/ad/suite/canonmedical/sup201512/session1-1]

Non-patent document 2: Yanbo Zhang, Hengyong Yu, "Convolutional Neural Network Based Metal Artifact Reduction in X-Ray Computed Tomography," [online], [retrieved on Jul. 3, 2019], Internet: [URL: https://arxiv.org/abs/1709.01581]

SUMMARY OF THE INVENTION

Problems to be Solved by the Invention

However, in the prior art, it was not possible to precisely obtain a positive bioimage with few defects from a negative bioimage having defects such as metal artifacts.

Further, the technique adopted in the above-mentioned prior art is supervised learning, and in such supervised learning, an image having few defects corresponding to an image having defects is required, but generally in bioimages, it is difficult to obtain such an image pair.

Means to Solve the Above Problems

A bioimage acquiring device according to a first embodiment of the invention comprises a classifier storage unit that stores a classifier that determines whether a bioimage is a negative bioimage or a positive bioimage, wherein the classifier is created using one or more negative bioimages which are defective bioimages and one or more positive bioimages which are non-defective bioimages, a converter storage unit that stores a first converter used for a conversion process to acquire a positive bioimage from a negative bioimage, and a negative bioimage receiving unit that receives negative bioimages, a first conversion unit that performs a first conversion process of converting a negative bioimage received by the negative bioimage receiving unit using a first converter, and acquiring a converted bioimage which is the conversion result, and a classifying unit that performs a first classifying process using the classifier for determining whether the converted bioimage acquired by the first conversion unit is a positive bioimage or a negative bioimage, wherein the first conversion unit performs a learning process using the determination result of the classifying unit and the converted bioimage, and performs an update process for updating the first converter, the negative bioimage receiving unit receives a new negative bioimage, and the first conversion unit converts a new negative bioimage received by the negative bioimage receiving unit using the updated first converter, and acquires a converted bioimage which is the conversion result.

According to this configuration, a positive bioimage with few defects can be acquired from a negative bioimage with defects such as metal artifacts, with high precision and without using teacher data.

A bioimage acquiring device according to a second embodiment of the invention is identical to that of the first embodiment, but further comprising a bioimage storage unit that stores the one or more negative bioimages and one or more positive bioimages, and a learning unit that generates a classifier used for determining whether the received bioimage is a positive bioimage or a negative bioimage using, in addition to the one or more negative bioimages and one or more positive bioimages of the bioimage storage unit, one or more converted bioimages acquired by the first conversion unit as negative bioimages.

According to this configuration, by precisely determining whether the bioimage is a positive bioimage or a negative bioimage, a positive bioimage with few defects can be acquired from a negative bioimage with defects such as metal artifacts, with high precision and without using teacher data.

A bioimage acquiring device according to a third embodiment of the invention is identical to that of the first or second embodiment, but further comprising a feature amount vector acquiring unit that acquires an input feature amount vector which is one or more features of the negative bioimage supplied to the first conversion unit and an output feature amount vector which is one or more features of the converted bioimage acquired by the first conversion unit, and a feature amount difference information acquiring unit that acquires feature amount difference information relating to the difference between the input feature amount vector and the output feature amount vector, wherein the first conversion unit performs a learning process so that the feature amount difference information is reduced, and updates the first converter.

According to this configuration, a positive bioimage with few defects that retains the features of the negative bioimage can be acquired with high precision from a negative bioimage with defects such as metal artifacts, without using teacher data.

A bioimage acquiring device according to a fourth embodiment of the invention is identical to that of any of the first to third embodiments, wherein the converter storage unit further comprises a second conversion unit that stores a second converter used for a conversion process for acquiring a negative bioimage from a positive bioimage that converts the converted bioimage acquired by the first conversion unit using the second converter and performs a second conversion process to acquire a second converted bioimage which is the conversion result, the first conversion unit converts the second converted bioimage acquired by the second conversion unit using the first converter, and the classifying unit performs a second classifying process for determining whether the converted bioimage acquired by the first conversion unit from the second converted bioimage is a positive bioimage or a negative bioimage, further comprising a control unit that performs control such that the first conversion process, the first classifying process, the second conversion process, and the second classifying process are performed once, twice or more.

According to this configuration, a positive bioimage with few defects that retains the features of the negative bioimage can be obtained from a negative bioimage with defects such as metal artifacts with high precision, and without using teacher data.

The bioimage acquiring device according to a fifth embodiment of the invention is identical to that of the fourth embodiment, but further comprising a feature amount vector acquiring unit that acquires a feature amount vector of at least two of a converted bioimage which is an input to the second conversion unit, a second converted bioimage which is an output of the second conversion unit, and a converted bioimage which is an output for the second converted bioimage from the first conversion unit, and a feature amount difference information acquiring unit that acquires feature amount difference information relating to the difference between at least one pair of two or more feature amount vectors which are acquired by the feature amount vector acquiring unit, wherein the first conversion unit performs a learning process so that the feature amount difference information is reduced, and updates the first converter.

According to this configuration, a positive bioimage with few defects that retains the features of the negative bioimage can be obtained from a negative bioimage with defects such as metal artifacts with high precision, and without using teacher data.

The bioimage acquiring device according to a sixth embodiment of the invention is identical to that of any of the first to fifth embodiments, wherein the negative bioimage is a set of two or more slice images obtained by cutting a part of a defective image set of an imaged living body into round slices, and the positive bioimage is a set of two or more slice images obtained by cutting a part of a non-defective image set of the imaged living body into round slices.

According to this configuration, a three-dimensional positive bioimage with few defects can be obtained from a negative bioimage with defects such as metal artifacts with high precision, and without using teacher data.

The bioimage acquiring device according to a seventh embodiment of the invention is identical to that of any of the first to sixth embodiments, wherein the first conversion unit performs a first conversion process only for pixels having a pixel value in a predetermined range, and the classifying unit performs a first classifying process for determining whether the image that is acquired by the first conversion unit is a positive bioimage or a negative bioimage, using a classifier created for only pixels having a pixel value in the predetermined range.

According to this configuration, a positive bioimage of a tissue with few defects can be obtained from a negative bioimage of a tissue such as bone with defects such as metal artifacts with high precision, and without using teacher data.

The bioimage acquiring device according to an eighth embodiment of the invention is identical to the bioimage acquiring device of the seventh embodiment, wherein the pixels having a pixel value in a predetermined range are pixels constituting a bone image.

According to this configuration, a positive bioimage of a bone part with few defects can be obtained from a negative bioimage of a bone part with defects such as metal artifacts with high precision, and without using teacher data.

The bioimage acquiring device according to a ninth embodiment of the invention is identical to that of any of the first to eighth embodiments, further comprising a bioimage receiving unit that receives two or more bioimages, wherein the classifying unit uses a classifier to determine whether each of the two or more bioimages received by the bioimage receiving unit is a positive bioimage or a negative bioimage, and the negative bioimage receiving unit acquires a bioimage determined to be a negative bioimage by the classifying unit.

According to this configuration, since processing is performed only on the negative bioimages among the received bioimages, a set of positive bioimages can be acquired rapidly with high precision and without using teacher data.

The converter generating device according to a tenth embodiment of the invention is a device that generates a converter of any of the first to ninth embodiments, comprising a bioimage storage unit that stores the one or more negative bioimages supplied to the bioimage acquiring device, and the one or more converted bioimages acquired by the first conversion unit of the bioimage acquiring device, a learning unit that acquires a converter used to acquire a positive bioimage, which is a converted bioimage, from a negative bioimage using the one or more negative bioimages and the one or more converted bioimages of the bioimage storage unit, and a converter accumulation unit that accumulates the converter acquired by the learning unit.

According to this configuration, a highly precise converter for acquiring a positive bioimage from a negative bioimage can be automatically acquired.

The bioimage acquiring device according to an eleventh embodiment of the invention is identical to that of the tenth embodiment, but comprising a converter storage unit in which the converter acquired by the converter generating device is stored, a negative bioimage receiving unit that receives a negative bioimage, a conversion unit that converts the negative bioimage received by the negative bioimage receiving unit using the converter of the converter storage unit and acquires a positive bioimage which is the conversion result, and an output unit that outputs the positive bioimage acquired by the conversion unit.

According to this configuration, a positive bioimage can be acquired from a negative bioimage with high precision and without using teacher data by using an automatically acquired highly precise converter.

Advantageous Effects of the Invention

In the bioimage acquiring device according to the present invention, a positive bioimage with few defects can be acquired with high precision from a negative bioimage having defects such as metal artifacts without using teacher data.

DESCRIPTION OF THE PREFERRED EMBODIMENTS

Figure 1:
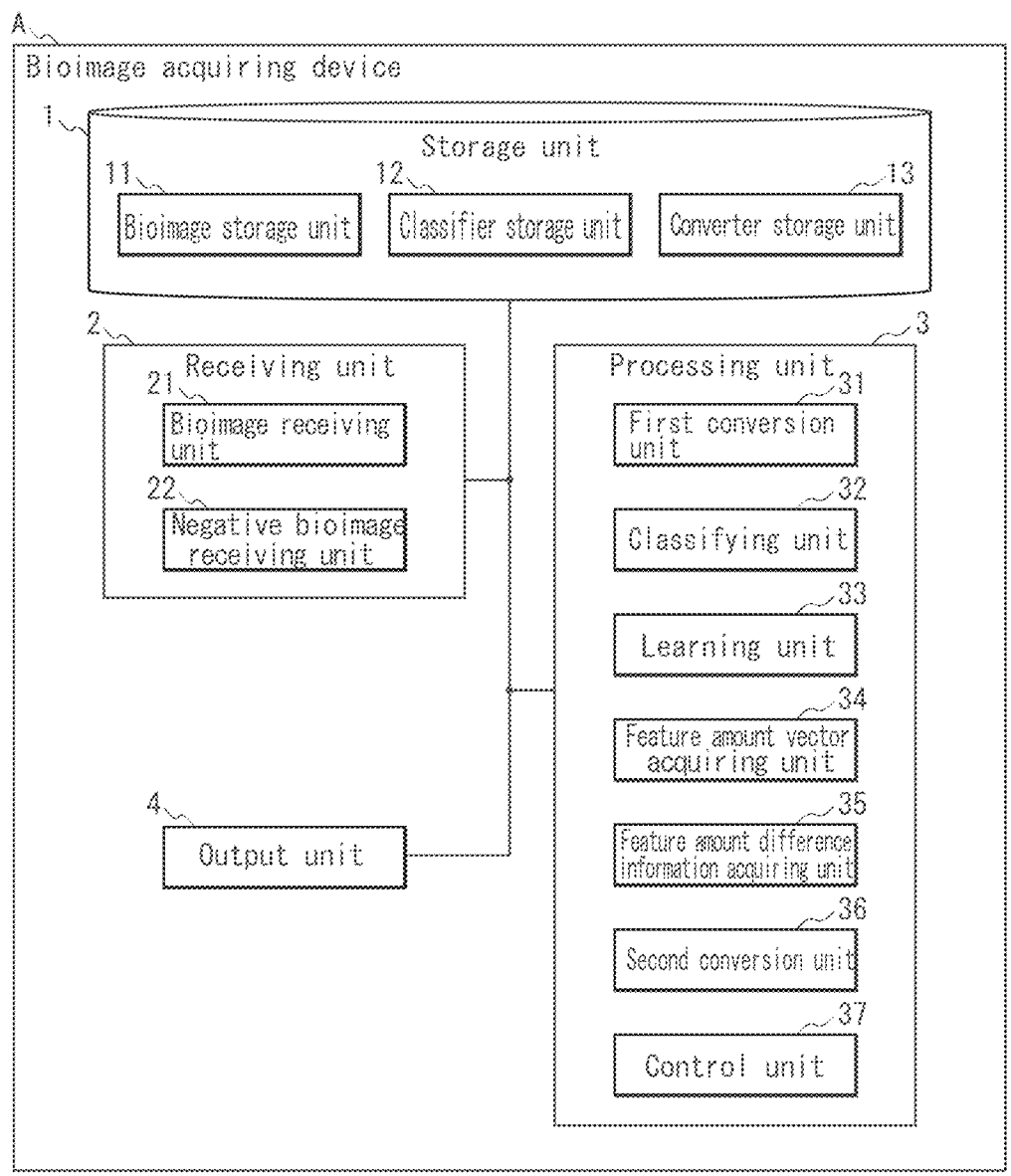
FIG. 1 is a block diagram of a bioimage acquiring device A according to a first embodiment.

Hereinafter, specific embodiments of the bioimage acquiring device and the like will be described referring to the drawings. In the embodiments, components with the same reference signs perform the same function, and their description may not be repeated.

Embodiment 1

According to the present embodiment, a bioimage acquiring device will be described that generates a positive bioimage, which is a bioimage with few defects, from a negative bioimage which is a defective bioimage. The bioimage may be called a medical image. A bioimage is an image obtained from a living body. A bioimage is usually one, two or more still images obtained by photographing a living body. The part of the living body from which the bioimage can be obtained is not particularly limited. The part is, for example, the oral cavity. The bioimage is, for example, a CT image obtained from a living body such as a human or a horse using X-ray CT, an MRI image obtained from a living body using MRI, or a PET image obtained from a living body using PET. It will be understood that the positive bioimage may be a bioimage without defects. Further, the defective bioimage is, for example, a bioimage having a metal artifact, a bioimage in which a soft tissue region is disturbed, or a bioimage in which a bone tissue is defective. The bioimage in which the soft tissue region is disturbed may be a bioimage in which the CT value of the nearby soft tissue is not correctly configured due to the influence of metal. Moreover, a defective bioimage of bone tissue is, for example, a bioimage including a part of the bone when the CT value of part of the bone is lowered due to infiltration of a tumor, and there is a defect when it is visualized.

According to the present embodiment, a bioimage acquiring device will be described comprising a first conversion unit in which a classifier is stored for classifying whether the received bioimage is a positive bioimage or a negative bioimage by using one or more negative bioimages and one or more positive bioimages, that converts the received negative bioimage and which acquires the converted bioimage which is the conversion result, and which determines whether the converted bioimage is a positive bioimage or a negative bioimage using the classifier, wherein the first conversion unit learns the converted bioimage and the determination result, converts the negative bioimage using the first conversion unit after learning, and acquires the converted bioimage.

According to the present embodiment, a bioimage acquiring device will be described further comprising a learning unit in which one or more negative bioimages and one or more positive bioimages are stored, which reconfigures the classifier using the converted bioimage acquired by the first conversion unit as a negative bioimage.

According to the present embodiment, a bioimage acquiring device will be described wherein information on the difference between one or more feature amounts of the negative bioimage supplied to the first conversion unit and one or more feature amounts of the converted bioimage acquired by the first conversion unit, is acquired, and the first conversion unit learns so that the difference information is reduced.

According to the present embodiment, a bioimage acquiring device will be described comprising a second conversion unit which performs an inverse conversion process on the converted bioimage to generate a positive bioimage, and performing a cyclic conversion such that the converted bioimage generated by the second conversion unit is supplied to the first conversion unit as a negative bioimage.

According to the present embodiment, a bioimage acquiring device will be described wherein information on the difference between one or more feature amounts of the converted bioimage supplied to the second conversion unit and one or more feature amounts of the converted bioimage generated by the second conversion unit is acquired, and the first conversion unit learns so that the difference information is reduced.

According to the present embodiment, a bioimage acquiring device will be described wherein the first conversion unit and the classifying unit perform processing only on pixels having a pixel value in a predetermined range among the pixels of the negative bioimage and the positive bioimage (for example, only the pixels in a bone region).

According to the present embodiment, a bioimage acquiring device will be described wherein the image conversion process is performed only on a negative bioimage selected by the user or only an automatically selected negative bioimage among two or more stored bioimages.

Further, in the present embodiment, the negative bioimage to be converted once and the generated positive bioimage may be a set of two or more slice images.

FIG. 1 is a block diagram of a bioimage acquiring device A according to the present embodiment. The bioimage acquiring device A comprises a storage unit 1, a receiving unit 2, a processing unit 3, and an output unit 4.

The storage unit 1 comprises, for example, a bioimage storage unit 11, a classifier storage unit 12, and a converter storage unit 13. The receiving unit 2 comprises, for example, a bioimage receiving unit 21 and a negative bioimage receiving unit 22. The processing unit 3 comprises, for example, a first conversion unit 31, a classifying unit 32, a learning unit 33, a feature amount vector acquiring unit 34, a feature amount difference information acquiring unit 35, a second conversion unit 36, and a control unit 37.

Various types of information can be stored in the storage unit 1. The various types of information are, for example, bioimages. The bioimage is a negative bioimage or a positive bioimage described later. Various types of information are, for example, a classifier described later and a converter described later.

One, two or more bioimages are stored in the bioimage storage unit 11. It is preferred that the bioimage storage unit 11 stores one, two or more negative bioimages, and one two or more positive bioimages.

The two or more negative bioimages may be a set of two or more slice images obtained by cutting part of a set of bioimages which are the result of photographing a living body, into round slices. Further, the two or more positive bioimages may be a set of two or more slice images obtained by cutting part of a set of bioimages which are the result of photographing a living body, into round slices. Further, the set of two or more slice images may be a set of two or more slice images that are spatially continuous, or a set of two or more slice images that are spatially separated.

The classifier is stored in the classifier storage unit 12. The classifier may be called a learning device. The classifier is information used to determine whether the bioimage to be classified is a negative bioimage or a positive bioimage. The classifier here is a classifier created by using one or more negative bioimages and one or more positive bioimages. Classifiers are usually created by machine learning algorithms. Various image classification algorithms are commonly available for creating classifiers. Specifically, the algorithm used in the machine learning for the process of creating the classifier and the machine learning described later is not particularly limited. For machine learning, for example, deep learning, SVR, random forest, decision tree and the like can be used. Further, in machine learning, in order to configure a classifier, a classifier can for example be obtained by supplying an input information group as an argument to a machine learning function. Machine learning functions comprise, for example, TensorFlow functions, TinySVM, and various Random Forest functions. The input information group is, for example, one or more negative bioimages and information showing negative bioimages, and one or more positive bioimages and information showing positive bioimages.

As regards prediction (classification) in machine learning, if a classifier and an information group to be input are supplied to the machine learning function as arguments, predicted information can be obtained. The classifier of the classifier storage unit 12 is, for example, information acquired by the learning unit 33, described later. The information group to be input is, for example, a bioimage. Further, the predicted information here is information for specifying, for example, whether it is a negative bioimage or a positive bioimage.

The first converter is stored in the converter storage unit 13. The second converter is also stored in the converter storage unit 13.

The first converter is a converter used for a conversion process for acquiring a positive bioimage from a negative bioimage. The conversion process for acquiring a positive bioimage is a process for acquiring a bioimage having few defects or no defects from a defective bioimage. The first converter is, for example, information having a neural network structure acquired by a deep learning algorithm. The neural network structure is, for example, CNN (Convolution Neural Network), AutoEncoder, RNN (Recurrent Neural Network). The first converter can be implemented by, for example, a 2D or 3D convolution function, a pooling function, an activation function, or the like. Further, using a CNN converter, the image after conversion is obtained by performing, for example, the three processes of (1) convolution, (2) pooling, and (3) activation once, twice or more on the received image.

The second converter is a converter used for a conversion process for acquiring a negative bioimage from a positive bioimage. The second converter is, for example, information having a neural network structure acquired by a deep learning algorithm. The neural network structure is, for example, CNN (Convolution Neural Network), AutoEncoder, or RNN (Recurrent Neural Network). The second converter can also be implemented by a 2D or 3D convolution function, a pooling function, an activation function, or the like, similarly to the first converter. Using a CNN converter, the image after conversion is obtained by performing the three processes of (1) convolution, (2) pooling, and (3) activation once, twice or more on the received image. Note that the learning process for configuring the first converter and the second converter may be performed by the processing unit 3 or by an external device, not shown. Since the learning process for configuring the first converter and the second converter is a known technique in the art, a detailed description thereof is omitted.

The receiving unit 2 receives various instructions, information, and the like. The various instructions, information, and the like are, for example, one, two or more bioimages, or one, two or more negative bioimages. Here, receiving is a concept that comprises the receiving of information input from an input device such as a keyboard, a mouse, or a touch panel, receiving information transmitted via a wired or wireless communication line, and receiving information read from a recording medium such as an optical disk, a magnetic disk, a semiconductor memory, or the like.

The input means for inputting various instructions and information and the like may be any means such as a touch panel, a keyboard, a mouse, or a menu screen.

The bioimage receiving unit 21 receives two or more bioimages. Such two or more bioimages usually comprise a negative bioimage and a positive bioimage.

The negative bioimage receiving unit 22 receives one, two or more negative bioimages. The negative bioimage receiving unit 22 receives, for example, one, two or more new bioimages. The negative bioimage receiving unit 22 acquires, for example, a bioimage determined by the classifying unit 32 to be a negative bioimage.

The processing unit 3 performs various processes. The various processes are, for example, processes performed by the first conversion unit 31, the classifying unit 32, the learning unit 33, the feature amount vector acquiring unit 34, the feature amount difference information acquiring unit 35, the second conversion unit 36, and the control unit 37.

The first conversion unit 31 converts the negative bioimage received by the negative bioimage receiving unit 22 using the first converter, and performs the first conversion process to acquire the converted bioimage which is the conversion result. The converted bioimage is usually a bioimage having fewer defects than the negative bioimage to be processed. The converted bioimage acquired by performing the first conversion process a small number of times such as once or twice, may not be a positive bioimage without defects. The first conversion process is, for example, a process using a deep learning algorithm. The first conversion process may, for example, be a process of forward propagation of deep learning. Alternatively, the first conversion process may, for example, be a process of repeating forward propagation and back propagation of deep learning. However, the first conversion process may be a process using an algorithm such as AutoEncoder, U-Net, Res-Net, or style conversion (Adaptive Instance Normalization).

The first conversion unit 31 performs a learning process using the determination result obtained by the classifying unit 32 and the converted bioimage, and updates the first converter. Such a process may be called an update process. The update process is, for example, a deep learning back propagation process. The update process may, for example, be a process of repeating forward propagation and back propagation of deep learning. However, the update process may be a process using an algorithm such as gradient descent or steepest descent.

The first conversion unit 31 converts a new negative bioimage received by the negative bioimage receiving unit 22 using the updated first converter, and acquires a converted bioimage which is the conversion result, for example.

It is preferred that the first conversion unit 31 performs a learning process so that the feature amount difference information is reduced, and updates the first converter, for example. The feature amount difference information is the feature amount difference information acquired by the feature amount difference information acquiring unit 35, described later. Performing the learning process so that the feature amount difference information is reduced means supplying the feature amount difference information as a loss to the first conversion unit 31, and performing the update process of the first converter. The first conversion unit 31 adds feature amount difference information as a loss as preprocessing for performing back propagation, and performs back propagation, for example. The first conversion unit 31 performs back propagation by adding feature amount difference information to the loss acquired by forward propagation, for example.

The first conversion unit 31 converts the second converted bioimage acquired by the second conversion unit 36 using the first converter, and acquires the converted bioimage which is the conversion result, for example.

The first conversion unit 31 may perform the first conversion process only for pixels having a pixel value in a predetermined range. A pixel having a pixel value in a predetermined range is, for example, a pixel having a pixel value in a specific part or region. Pixels with pixel values in a predetermined range are, for example, pixels that constitute an image of a bone. When the bioimage is a CT image, the pixel values of the pixels constituting the bone image are, for example, 100 to 500. The pixels having a pixel value in a predetermined range are, for example, pixels having a pixel value in a soft tissue region.

The classifying unit 32 uses the classifier of the classifier storage unit 12 to perform a first classifying process for determining whether the converted bioimage acquired by the first conversion unit 31 is a positive bioimage or a negative bioimage.

The classifying unit 32 may perform a second classifying process for determining whether the converted bioimage acquired by the first conversion unit 31 from the second converted bioimage is a positive bioimage or a negative bioimage.

The classifying unit 32 performs a first classifying process to determine whether the converted bioimage acquired by the first conversion unit 31 is a positive bioimage or a negative bioimage using a classifier created for only pixels having a pixel value in a predetermined range, for example.

The classifying unit 32 uses the classifier of the classifier storage unit 12 to determine whether each of the two or more bioimages received by the bioimage receiving unit 21 is a positive bioimage or a negative bioimage, for example.

The algorithm of the classifying process performed by the classifying unit 32 is not particularly limited. The classifying unit 32 performs classifying processing by an algorithm such as deep learning, SVM, decision tree, or random forest, for example.

The classifying unit 32 may use the Wasserstein distance, which is a known technique, to determine whether each of the two or more bioimages received by the bioimage receiving unit 21 is a positive bioimage or a negative bioimage. In this case, the classifying unit 32 precisely measures the distance, and the conversion unit 31 learns to convert a first group of images A (e.g., negative bioimages) to a second group of images (e.g., positive bioimages) by attempting to reduce the distance acquired by the classifying unit 32. The learning unit 33 generates a classifier used to determine whether the received bioimage is a positive bioimage or a negative bioimage using, in addition to one or more negative bioimages and one or more positive bioimages of the bioimage storage unit 11, one or more converted bioimages acquired by the first conversion unit 31 as negative bioimages.

The learning unit 33 generates the classifier by using the one or more negative bioimages and one or more positive bioimages stored in the bioimage storage unit 11, for example. The learning unit 33 generates the classifier using one or more negative bioimages and information indicating that they are negative bioimages, and one or more positive bioimages and information indicating that they are positive bioimages, stored in the bioimage storage unit 11, for example.

The process by which the learning unit 33 generates a classifier is usually implemented by a machine learning algorithm. The machine learning algorithm may be deep learning, SVM, decision tree, random forest, or the like.

The feature amount vector acquiring unit 34 acquires the feature amount vector of at least two or more of the converted bioimages from among the converted bioimage that is input to the second conversion unit 36, the second converted bioimage which is the output of the second conversion unit 36, and the converted bioimage which is the output of the first conversion unit 31 with respect to the second converted bioimage. The feature amount vector is a set of feature amounts of the image. The feature amount of the image is, for example, the pixel value, the difference between the pixel values of the pixels at two predetermined positions, the average value of a predetermined number of pixel values in a predetermined area, and the difference between pixel values at the same position in a spatial direction (z-axis direction) of two bioimages. The content of the feature amount of the image is not particularly limited.

Since the process of acquiring the feature amount vector from an image is a known technique in the art, a detailed description thereof is omitted.

The feature amount vector acquiring unit 34 acquires an input feature amount vector which is one or more feature amounts of a negative bioimage supplied to the first conversion unit 31, and an output feature amount vector which is one or more feature amounts of the converted bioimage acquired by the first conversion unit 31.

The feature amount difference information acquiring unit 35 acquires feature amount difference information relating to the difference between one or more pairs of the two or more feature amount vectors acquired by the feature amount vector acquiring unit 34. The feature amount difference information is, for example, the distance between two or more feature amount vectors. The feature amount difference information is, for example, the absolute value of the difference between two or more feature amount vectors.

The feature amount difference information acquiring unit 35 acquires feature amount difference information relating to the difference between the input feature amount vector and the output feature amount vector, for example.

The second conversion unit 36 converts the converted bioimage acquired by the first conversion unit 31 using the second converter, and performs a second conversion process to acquire the second converted bioimage which is the conversion result. The second conversion process is, for example, a forward propagation process of deep learning. The second conversion process is, for example, a process of repeating forward propagation and back propagation of deep learning. However, the second conversion process may be a process using an algorithm such as AutoEncoder, U-Net, Res-Net, or style conversion (Adaptive Instance Normalization).

The control unit 37 performs control so that the first conversion process, the first classifying process, the second conversion process, and the second classifying process are performed once, twice or more. The control unit 37 performs control to repeat the first conversion process, the first classifying process, the second conversion process, and the second classifying process until a predetermined termination condition is satisfied, for example. The predetermined termination condition is, for example, that the series of processes of the first conversion process, the first classifying process, the second conversion process, and the second classifying process are executed N (N is an integer equal to 1 or more) times. Alternatively, the termination condition is, for example, that a converted bioimage having a ratio equal to or higher than a threshold value (for example, 100%, or 95% or higher) is determined to be a positive bioimage.

The output unit 4 outputs various information. The various information is converted bioimages acquired by the first conversion unit 31, for example. The output unit 4 stores the converted bioimages acquired by the first conversion unit 31 in the storage unit 1, for example.

Here, output means display on a display, projection using a projector, printing by a printer, sound output, transmission to an external device, storage in a recording medium, or transfer of the processing result to another processing device, program, or the like.

The storage unit 1, the bioimage storage unit 11, the classifier storage unit 12, and the converter storage unit 13 are preferably non-volatile recording media, but can also be implemented by volatile recording media.

The process of storing information in the storage unit 1 or the like is not particularly limited. For example, information may be stored in the storage unit 1 or the like via a recording medium, or information transmitted via a communication line or the like may be stored in the storage unit 1 or the like. Alternatively, information input via an input device may be stored in the storage unit 1 or the like.

The receiving unit 2, the bioimage receiving unit 21 and the negative bioimage receiving unit 22 can be implemented by, for example, a device driver of an input means such as a touch panel or a keyboard, menu screen control software, or the like.

The processing unit 3, the first conversion unit 31, the classifying unit 32, the learning unit 33, the feature amount vector acquiring unit 34, the feature amount difference information acquiring unit 35, the second conversion unit 36, and the control unit 37 are usually implemented by MPUs or memories. The processing procedure of the processing unit 3 and the like is usually implemented by software, and the software is recorded on a recording medium such as a ROM. However, it may be implemented by hardware (a dedicated circuit).

The output unit 4 may or may not comprise an output device such as a display or a speaker. The output unit 4 can be implemented by driver software of the output device, or driver software of the output device and the output device, or the like.

Next, an operation example of the bioimage acquiring device A will be described referring to the flowchart of FIG. 2.

(Step S201) The bioimage receiving unit 21 determines whether or not one or more bioimages have been received. If one or more bioimages have been received, the routine proceeds to step S202, and if one or more bioimages have not been received, the routine returns to step S201.

(Step S202) The classifying unit 32 performs a classifying process on the one or more bioimages received in step S201. An example of the classifying process will be described referring to the flowchart of FIG. 3.

(Step S203) The first conversion unit 31 and the like perform a converter learning process. An example of the converter learning process will be described referring to the flowchart of FIG. 4. The converter learning process is a process of updating the first converter stored in the converter storage unit 13. The converter learning process may be considered as a tuning process for improving the precision of the first converter.

(Step S204) The learning unit 33 and the like perform a classifier learning process. An example of the classifier learning process will be described referring to the flowchart of FIG. 5. The classifier learning process is a process of updating the classifier stored in the classifier storage unit 12. The classifier learning process may be considered as a tuning process for improving the precision of the classifier.

(Step S205) The control unit 37 determines whether or not to terminate the loop process that repeats the processes of steps S203 and S204 based on a predetermined termination condition. If it terminates, the routine proceeds to step S206, and if it does not terminate, the routine returns to step S203. The termination condition is, for example, that the processes of steps S203 and S204 are executed N (N is an integer equal to 1 or more) times. Alternatively, as the termination condition, for example in step S405 in the converter learning process, it may be determined that a converted bioimage equal to or higher than a threshold value (for example, 100%, or 95% or more) is a positive bioimage. Specifically, it may be determined that a converted bioimage equal to or higher than a threshold value (for example, 100%, or 95% or more) is a positive bioimage by a classifier that can precisely classify the presence or absence of defects provided in advance, or the like.

(Step S206) The first conversion unit 31 substitutes 1 in a counter i.

(Step S207) The first conversion unit 31 determines whether or not an i-th negative bioimage exists in the bioimage storage unit 11. If the i-th negative bioimage exists, the routine proceeds to step S208, and if the i-th negative bioimage does not exist, the routine proceeds to step S212.

(Step S208) The first conversion unit 31 acquires the i-th negative bioimage from the bioimage storage unit 11.

(Step S209) The first conversion unit 31 performs the first conversion process on the i-th negative bioimage acquired in step S208 by using the updated first converter, and acquires an i-th positive bioimage. Here, the i-th positive bioimage is preferably an image wherein defects such as metal artifacts are completely removed, but may also be an image wherein defects are reduced.

(Step S210) The output unit 4 stores the i-th positive bioimage in the storage unit 1. The output unit 4 may associate the i-th positive bioimage with the i-th negative bioimage and store it in the storage unit 1, or overwrite the i-th negative bioimage, and store the i-th positive bioimage in the storage unit 1.

(Step S211) The first conversion unit 31 increments the counter i by 1. The routine returns to step S207.

(Step S212) The control unit 37 determines whether or not all the learning processes have been completed. When all the learning processes have been completed, the routine is terminated, and when all the learning processes have not been completed, the routine returns to step S201. The control unit 37 determines that all the learning processes have been completed when, for example, any of the following termination conditions is met. The termination condition is, for example, that the processes shown in steps S201 to S211 are executed N (N is an integer equal to 1 or more) times. Alternatively, as the termination condition, for example in step S405 in the converter learning process, it may be determined that a converted bioimage equal to or higher than a threshold value (for example, 100%, or 95% or more) is a positive bioimage. Specifically, it may be determined that a converted bioimage equal to or higher than the threshold value (for example, 100%, or 95% or more) is a positive bioimage by a classifier that can precisely classify the presence or absence of defects provided in advance, or the like.

Figure 2:
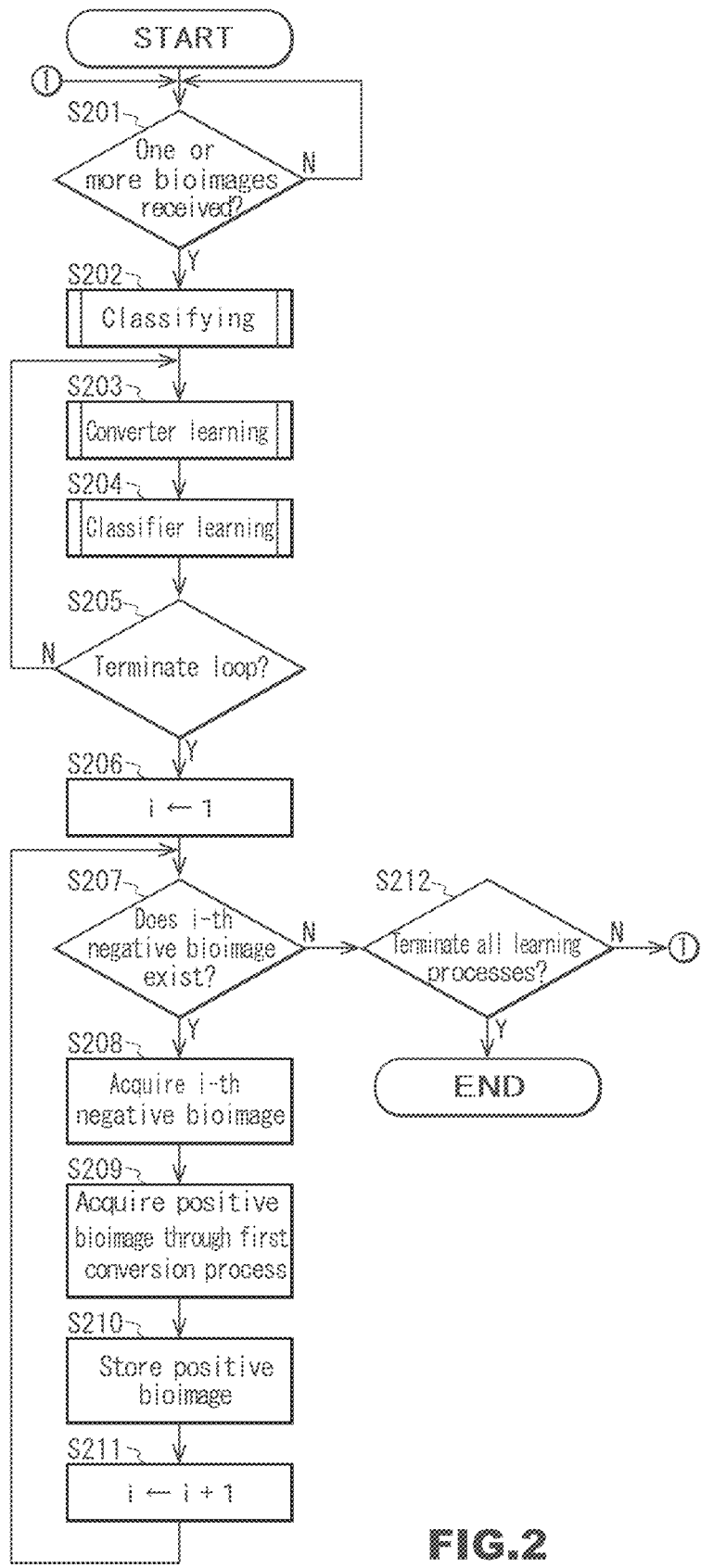
FIG. 2 is a flowchart illustrating an operation example of the bioimage acquiring device A according to a first embodiment.

In the flowchart of FIG. 2, in step S202, the process of classifying bioimages into negative bioimages and positive bioimages may be performed by a person. When a person performs the classifying process, the receiving unit 2 receives the judgment result of the person (information indicating whether the image is a positive bioimage or a negative bioimage), and the processing unit 3 associates the bioimage with the judgment result.

In the flowchart of FIG. 2, the process may be performed only for pixels of the bioimage having pixel values in a predetermined range. For example, when the bioimage is a CT image, only pixels having a pixel value of "100 to 500" may be acquired, and the first conversion unit 31 may perform the first conversion process and the classifying unit 32 may perform the first classifying process only for a bioimage of a bone region. In this case, for example, the processing unit 3 inspects the pixel value of each pixel of the bioimage to be processed, and leaves only the pixels having pixel values in the predetermined range (for example, it sets the values of other pixels to 0 or a maximum value, or the like).

Figure 3:
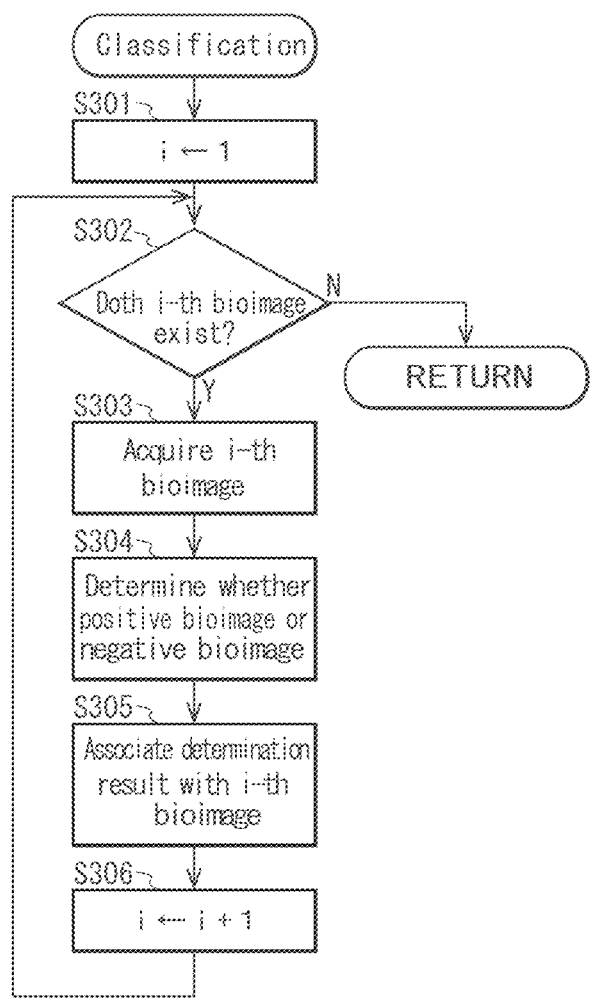
FIG. 3 is a flowchart describing an example of a classifying process according to a first embodiment.

Next, an example of the classifying process in step S202 will be described referring to the flowchart of FIG. 3.

(Step S301) The classifying unit 32 substitutes 1 in the counter i.

(Step S302) The classifying unit 32 determines whether or not the i-th bioimage exists in the bioimages received in step S201. If the i-th bioimage exists, the routine proceeds to step S303, and if the i-th bioimage does not exist, the routine returns to the preceding process.

(Step S303) The classifying unit 32 acquires the i-th bioimage.

(Step S304) The classifying unit 32 determines whether the i-th bioimage is a positive bioimage or a negative bioimage using the classifier of the storage unit 1, and acquires the determination result.

(Step S305) The classifying unit 32 associates the determination result acquired in step S304 with the i-th bioimage.

(Step S306) The classifying unit 32 increments the counter i by 1. The routine returns to step S302.

Next, an example of the converter learning process in step S203 will be described referring to the flowchart of FIG. 4.

(Step S401) The first conversion unit 31 substitutes 1 in the counter i.

(Step S402) The first conversion unit 31 determines whether or not the i-th negative bioimage exists. If the i-th negative bioimage exists, the routine proceeds to step S403, and if the i-th negative bioimage does not exist, the routine proceeds to step S411.

The i-th negative bioimage is, for example, the i-th negative bioimage among the bioimages determined to be negative bioimages in the classifying process of step S202.

Alternatively, the i-th negative bioimage may, for example, be the i-th negative bioimage among bioimages determined to be negative bioimages in the classifying process of step S202, and one or more converted bioimages acquired in the immediately preceding converter learning process.

(Step S403) The first conversion unit 31 acquires the i-th negative bioimage.

(Step S404) The first conversion unit 31 performs the first conversion process on the i-th negative bioimage using the first converter of the converter storage unit 13, acquires the i-th converted bioimage, and temporarily stores it in at least a buffer, not shown.

(Step S405) The classifying unit 32 performs the first classifying process on the i-th converted bioimage acquired in step S404, determines whether the i-th converted bioimage is a positive bioimage or a negative bioimage, and acquires the determination result.

(Step S406) The feature amount vector acquiring unit 34 acquires an input feature amount vector which is a set of two or more feature amounts of the i-th negative bioimage. Alternatively, the feature amount vector acquiring unit 34 acquires an output feature amount vector which is a set of two or more feature amounts of the i-th converted bioimage.

(Step S407) The feature amount difference information acquiring unit 35 acquires feature amount difference information relating to the difference between the input feature amount vector and the output feature amount vector acquired in step S406.

(Step S408) The first conversion unit 31 adds the feature amount difference information acquired in step S407 as a loss, and updates the loss relating to the first converter.

(Step S409) The first conversion unit 31 performs a learning process on the first converter of the converter storage unit 13 using the loss updated in step S408, and updates the first converter. Note that this process is a learning process of changing the first converter so that the feature amount difference information is reduced.

(Step S410) The first conversion unit 31 increments the counter i by 1. The routine returns to step S402.

(Step S411) The second conversion unit 36 substitutes 1 in the counter i.

(Step S412) The second conversion unit 36 determines whether or not the i-th converted bioimage exists among the converted bioimages temporarily stored in step S404. If the i-th converted bioimage exists, the routine proceeds to step S413, and if the i-th converted bioimage does not exist, the routine returns to the preceding process.

(Step S413) The second conversion unit 36 acquires the i-th converted bioimage from a buffer, not shown.

(Step S414) The second conversion unit 36 performs a second conversion process on the i-th converted bioimage acquired in step S413 using the second converter of the converter storage unit 13, and acquires an i-th converted bioimage. The converted bioimage acquired here may be referred to as a second converted bioimage.

(Step S415) The classifying unit 32 performs a classifying process on the i-th second converted bioimage acquired in step S414, determines whether the second converted bioimage is a positive bioimage or a negative bioimage, and acquires the determination result. Note that this process is a second classifying process.

(Step S416) The feature amount vector acquiring unit 34 acquires the feature amount vector of each of a pair of bioimages. The two paired bioimages are, for example, the i-th converted bioimage and the i-th second converted bioimage, or the i-th negative bioimage and the i-th second converted bioimage.

(Step S417) The feature amount difference information acquiring unit 35 acquires the feature amount difference information of the two feature amount vectors acquired in step S416.

(Step S418) The first conversion unit 31 updates the loss of the first converter using the feature amount difference information acquired in step S417.

(Step S419) The second conversion unit 36 performs a learning process using the loss acquired in step S418, and updates the first converter. Alternatively, the second conversion unit 36 performs a learning process on the second converter, and updates the second converter.

(Step S420) The second conversion unit 36 increments the counter i by 1. The routine returns to step S412.

Figure 4:
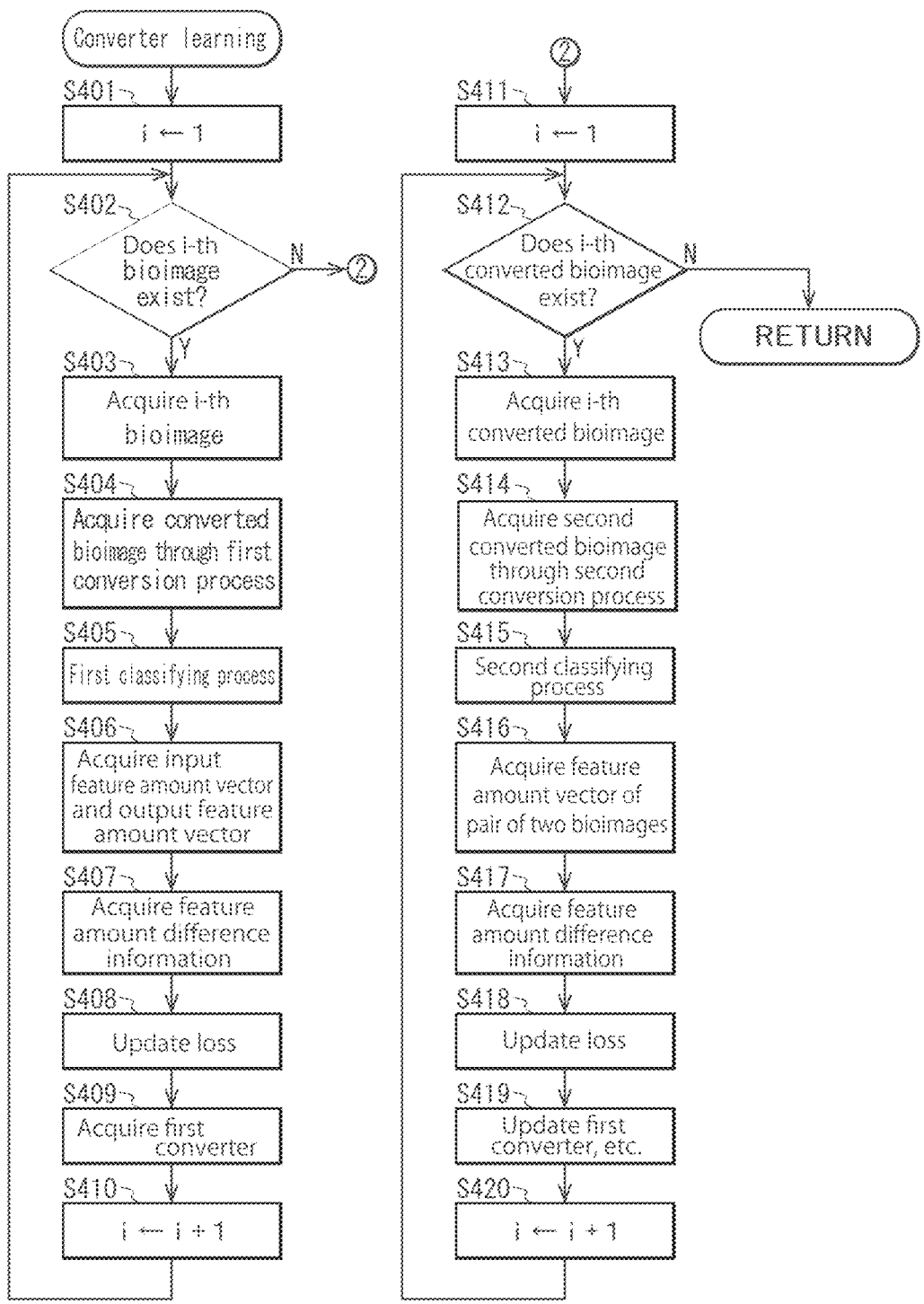
FIG. 4 is a flowchart describing an example of a converter learning process according to a first embodiment.

Note that, in the flowchart of FIG. 4, steps S411 to S420 may be omitted.

In the flowchart of FIG. 4, it is not necessary to add the feature amount difference information acquired in step S417 to the loss used for the update process of the first converter. Adding to the loss means, for example, a join process such as adding a feature difference to the loss obtained by forward propagation of the first converter by linear sum.

In the flowchart of FIG. 4, the update process of the first converter may be performed in combination with known techniques such as norm error, Gradient Penalty, and Wasserstein distance. Further, in the flowchart of FIG. 4, as described above, in the second and subsequent converter learning processes, one or more converted bioimages acquired in the immediately preceding converter learning process may also suitably be used as the negative bioimage.

Figure 5:
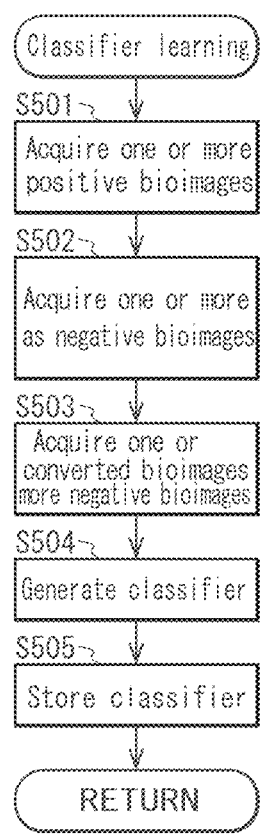
FIG. 5 is a flowchart describing an example of a classifier learning process according to a first embodiment.

Next, an example of the classifier learning process in step S204 will be described referring to the flowchart of FIG. 5.

(Step S501) The learning unit 33 acquires one or more positive bioimages from the bioimage storage unit 11.

(Step S502) The learning unit 33 acquires one or more converted bioimages acquired by the first conversion unit 31 as negative bioimages.

(Step S503) The learning unit 33 acquires one or more negative bioimages from the bioimage storage unit 11.

(Step S504) The learning unit 33 generates a classifier to classify images as positive or negative bioimages by a machine learning algorithm using the one or more positive bioimages acquired in step S501, and two or more negative bioimages acquired in steps S502 and S503. Here, the learning unit 33 may, instead of using the two or more negative bioimages acquired in step S503, generate a classifier to classify bioimages as positive bioimages or negative bioimages by a machine learning algorithm using the negative bioimages acquired in step S502.

(Step S505) The learning unit 33 stores the classifier generated in step S504 in the classifier storage unit 12. The routine returns to the preceding process. Note that the classifier is updated by this process.

Figure 6:
FIG. 6 is a figure showing an example of a negative bioimage according to a first embodiment.

Hereinafter, the specific operation of the bioimage acquiring device A according to the present embodiment will be described. In this specific example, the bioimage is, for example, a CT image. Negative bioimages are images with metal artifacts (e.g., FIG. 6). FIG. 6 is an image of the oral cavity of a human, but metal artifacts are produced by implants and dentures in the oral cavity, which make diagnosis and surgery by medical staff difficult. In the image of FIG. 6, a part which should be a soft tissue is partially hollow due to the detrimental effect of the metal artifacts.

In such a situation, two examples will be described. In Example 1, the bioimage is a slice image. In Example 2, the bioimage is a three-dimensional image which is a set of slice images.

Example 1

Figure 7:
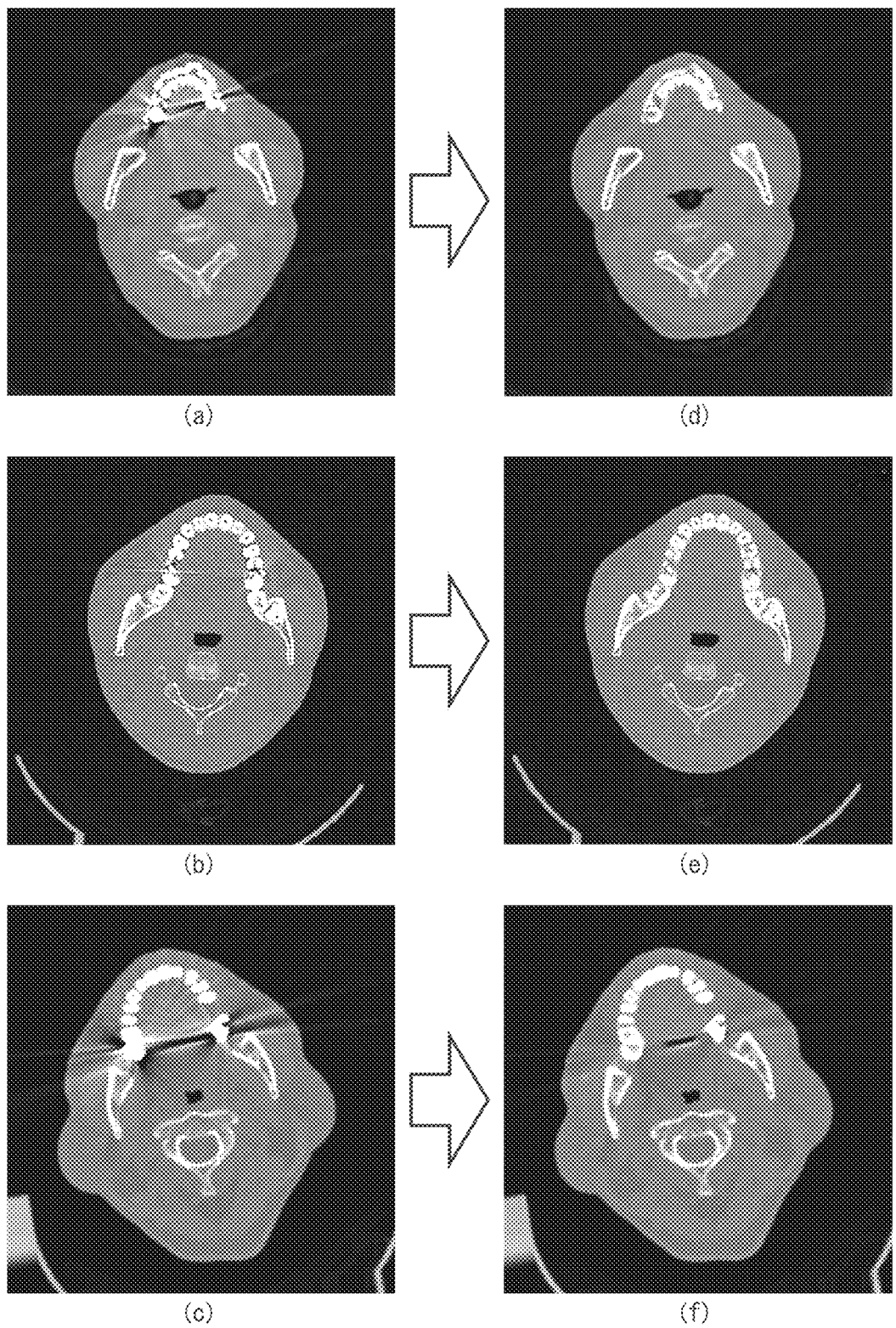
FIG. 7 is a figure describing the generation of a positive bioimage from a negative bioimage according to a first embodiment.

It will be assumed that the bioimage storage unit 11 of the bioimage acquiring device A stores negative bioimages such as (a), (b), and (c) of FIG. 7, and a large number of positive bioimages, not shown.

It will be assumed that the classifier storage unit 12 stores a classifier used for determining whether the bioimage is a negative bioimage or a positive bioimage.

It will be assumed that the converter storage unit 13 stores a first converter used for a conversion process for acquiring a positive bioimage from a negative bioimage. It will further be assumed that the converter storage unit 13 stores a second converter used for a conversion process for acquiring a negative bioimage from a positive bioimage.

In this situation, when the bioimage acquiring device A receives a processing start instruction, a classifying process is performed on the bioimages of the bioimage storage unit 11 using the classifier to classify them as positive bioimages and negative bioimages. It will be assumed that the bioimage acquiring device A has determined that bioimages such as (a), (b), and (c) in FIG. 7 are negative bioimages.

Next, the bioimage acquiring device A converts the negative bioimages of FIGS. 7 (a), (b), and (c) to FIGS. 7 (d), (e), and (f), respectively, by the processes described referring to the flowcharts of FIGS. 2 to 5, to obtain positive bioimages.

Note that the image of FIG. 7 (d) has few or no metal artifacts as compared with the image of FIG. 7 (a), and is filled with soft tissue, and the shape features of the oral cavity in FIG. 7(a) are retained. The image of FIG. 7 (e) has few or no metal artifacts as compared with the image of FIG. 7 (b), and the shape features of the oral cavity in the image of FIG. 7 (b) are retained. Further, the image of FIG. 7 (f) has few or no metal artifacts as compared to the image of FIG. 7 (c), is filled with soft tissue, and the shape features of the oral cavity in the image of FIG. 7 (c) are retained.

Example 2

Figure 8:
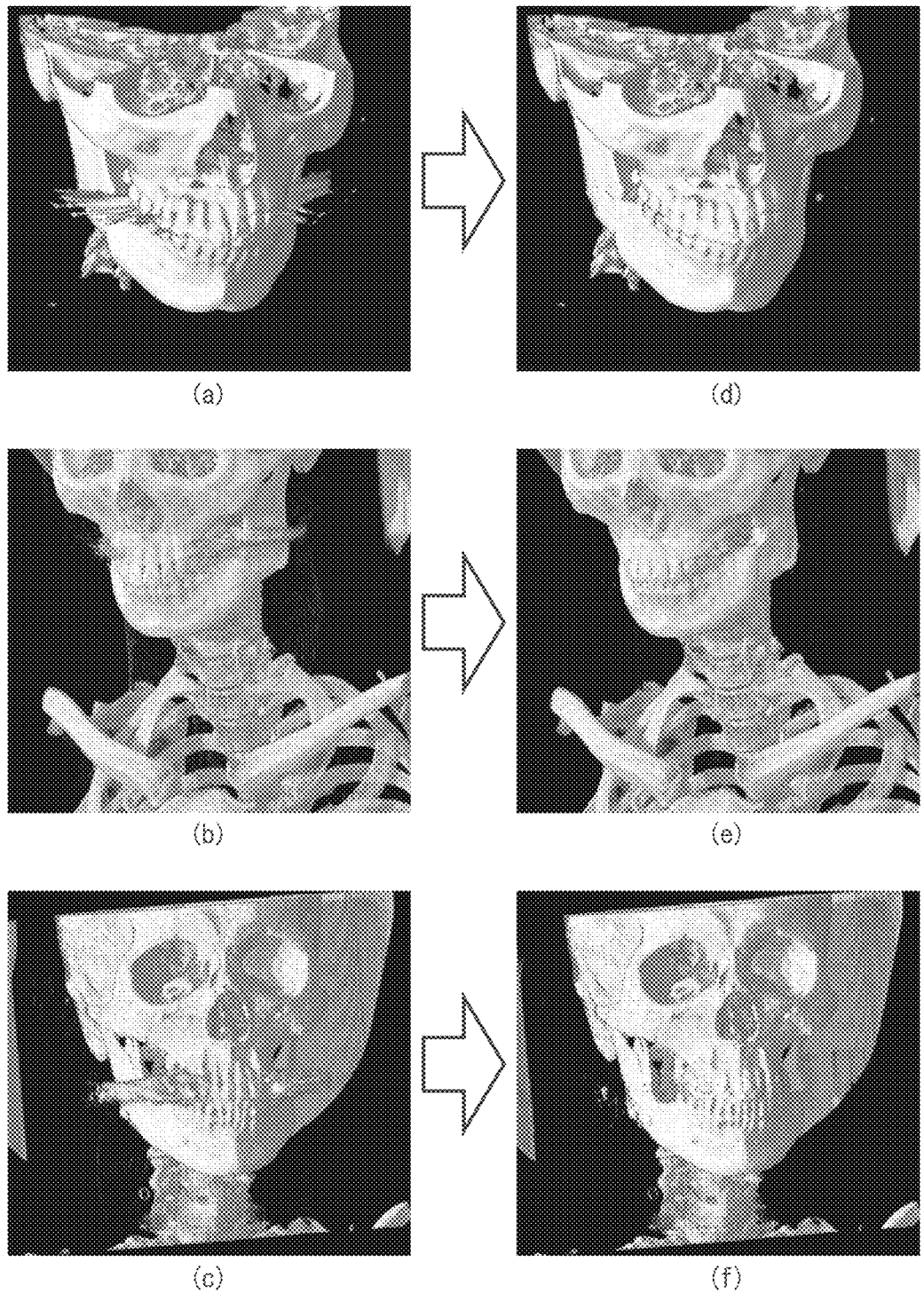
FIG. 8 is a figure describing the generation of a positive bioimage from a negative bioimage according to a first embodiment.

The bioimage storage unit 11 of the bioimage acquiring device A stores three-dimensional images including negative bioimages such as (a), (b), and (c) of FIG. 8, and a large number of positive bioimages, not shown. FIGS. 8 (a), (b), and (c) are three-dimensional images having a plurality of bioimages including still images having metal artifacts or the like. Further, FIGS. 8 (a), (b), and (c) are images wherein only pixels having a pixel value (100 to 500) in the range of a bone are represented.

The classifier storage unit 12 stores a classifier used for determining whether a set of one, two or more bioimages are negative bioimages or positive bioimages.

The converter storage unit 13 stores a first converter used for a conversion process for acquiring one, two or more positive bioimages from one, two or more negative bioimages. The converter storage unit 13 also stores a second converter used for a conversion process for acquiring one, two or more negative bioimages from one, two or more positive bioimages.

In this situation, when the bioimage acquiring device A receives a processing start instruction, it performs a classifying process on a set of two or more slice images constituting a three-dimensional bioimage in the bioimage storage unit 11 using a classifier, and performs a process to classify them into positive bioimages and negative bioimages. It will be assumed that the bioimage acquiring device A has determined, for example, that the set of two or more slice images constituting (a), (b), and (c) of FIG. 8 are negative bioimages.

Next, the bioimage acquiring device A converts the set of two or more slice images constituting (a), (b) and (c) of FIG. 8 by the processes described referring to the flowcharts of FIGS. 2 to 5, and acquires a set of two or more slice images without defects such as metal artifacts. The bioimage acquiring device A then constructs a three-dimensional image using the set of two or more acquired slice images. These three-dimensional images are (d), (e) and (f) of FIG. 8.

In the image of FIG. 8 (d), metal artifacts are reduced or eliminated as compared with the image of FIG. 8 (a), and the shape features of the oral cavity or the like in the image of FIG. 8 (a) are retained. In the image of FIG. 8 (e), metal artifacts are reduced or eliminated as compared with the image of FIG. 8 (b), and the shape features of the oral cavity, shoulder or the like in the image of FIG. 8 (b) are retained. Further, in the image of FIG. 8 (f), metal artifacts are reduced or eliminated as compared with the image of FIG. 8 (c), and the shape features of the oral cavity or the like in the image of FIG. 8 (c) are retained.

As described above, according to the present embodiment, a positive bioimage with few defects can for example be automatically acquired from a negative bioimage having defects such as metal artifacts without using teacher data.

According to the present embodiment, a positive bioimage with few defects can for example be automatically acquired from a negative bioimage having defects such as metal artifacts with high precision and without using teacher data.

According to the present embodiment, a positive bioimage having few defects that retains the features of the negative bioimage, can for example be automatically acquired from a negative bioimage having defects such as metal artifacts without using teacher data.

According to the present embodiment, a positive bioimage having few defects that retains the features of the negative bioimage, can for example be automatically acquired from a negative bioimage having defects such as metal artifacts with high precision, and without using teacher data.

According to the present embodiment, a three-dimensional positive bioimage with few defects can for example be automatically acquired from a three-dimensional negative bioimage having defects such as metal artifacts without using teacher data.

According to the present embodiment, a positive bioimage of a bone part having few defects can for example be automatically acquired from a negative bioimage which is a bioimage having defects such as metal artifacts, and which is a bioimage of a bone part, without using teacher data.

Figure 9:
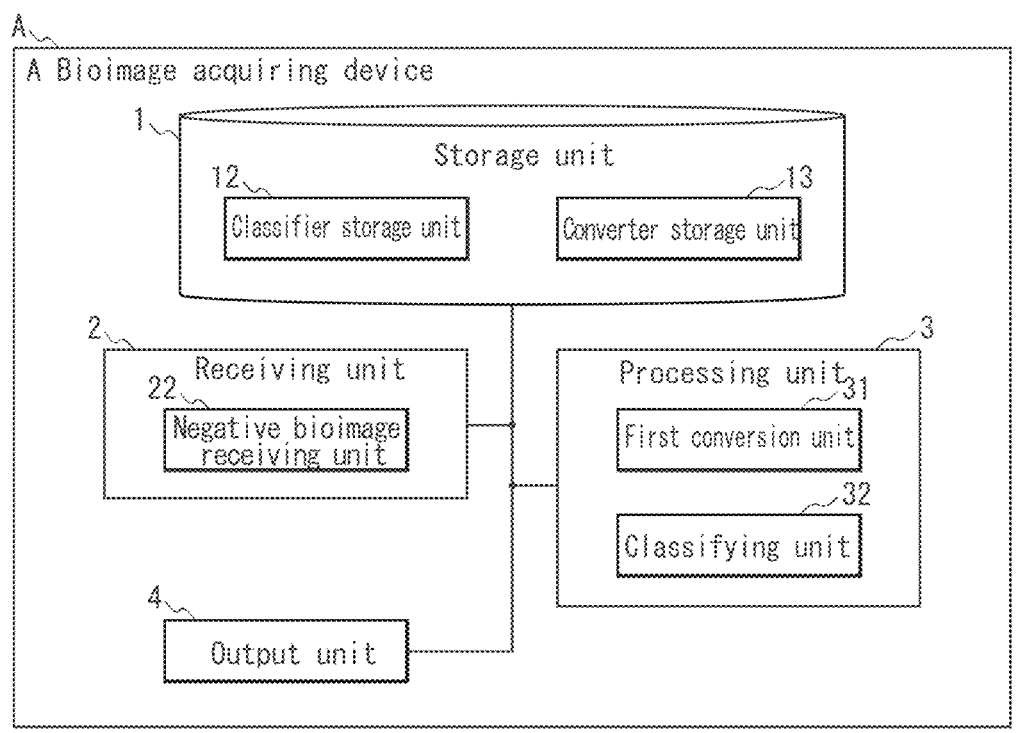
FIG. 9 is another example of a block diagram of the bioimage acquiring device A according to a first embodiment.

According to the present embodiment, the bioimage acquiring device A may have the minimum configuration as shown in FIG. 9. Specifically, the bioimage acquiring device A comprises a storage unit 1, a receiving unit 2, a processing unit 3, and an output unit 4. The storage unit 1 comprises a classifier storage unit 12 and a converter storage unit 13. The receiving unit 2 comprises a negative bioimage receiving unit 22. Further, the processing unit 3 comprises a first conversion unit 31 and a classifying unit 32.

The processing in the present embodiment may be implemented by software. This software may be distributed by software download or the like. Alternatively, this software may be recorded on a recording medium such as a CD-ROM, and distributed. Note that this also applies to the other embodiments herein. The software that implements the bioimage acquiring device A according to the present embodiment is the program described below. Specifically, the program causes a computer that can access a classifier storage unit that stores a classifier created by using one or more negative bioimages that are defective bioimages and one or more positive bioimages that are non-defective bioimages to determine whether the image is a negative bioimage or a positive bioimage, and a converter storage unit that stores a first converter used for a conversion process that attempts to acquire a positive bioimage from a negative bioimage, to function as a negative bioimage receiving unit that receives a negative bioimage, a first conversion unit that performs a first conversion process that acquires the converted bioimage which is the conversion result, and as a classifying unit that performs a first classifying process for determining whether the converted bioimage acquired by the first conversion unit is a positive bioimage or a negative bioimage, wherein the first conversion unit performs a learning process using the determination result of the classifying unit and the converted bioimage, and an update process for updating the first converter, the negative bioimage receiving unit receives a new negative bioimage, and the first conversion unit converts the new negative bioimage received by the negative bioimage receiving unit using the updated first converter, and acquires the converted bioimage which is the conversion result.

Embodiment 2

According to this embodiment, a converter component device that constitutes a first converter that performs a conversion process will be described wherein the one or more negative bioimages supplied to the bioimage acquiring device A described in the first embodiment are input, and one or more converted bioimages finally acquired by the bioimage acquiring device A are output.

Figure 10:
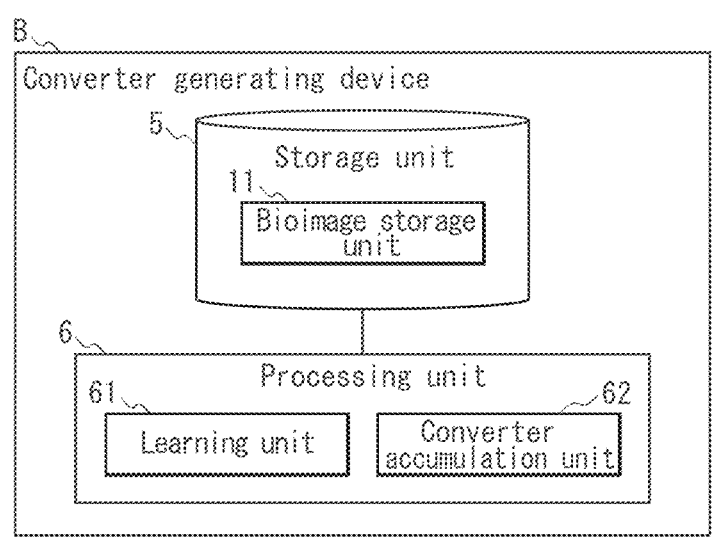
FIG. 10 is a block diagram of a converter generating device B according to a second embodiment.

FIG. 10 is a block diagram of a converter generating device B according to the present embodiment. The converter generating device B comprises a storage unit 5 and a processing unit 6. The storage unit 5 comprises a bioimage storage unit 11. The processing unit 6 comprises a learning unit 61 and a converter accumulation unit 62.

Various information is stored in the storage unit 5. The various information is, for example, one or more bioimages.

The bioimage storage unit 11 stores one or more negative bioimages supplied to the bioimage acquiring device A, and one or more converted bioimages acquired by the first conversion unit 31 of the bioimage acquiring device A. The one or more converted bioimages are converted bioimages finally acquired by the bioimage acquiring device A. It will be assumed that each of the one or more converted bioimages corresponds to a negative bioimage before conversion.

The processing unit 6 performs various processes. The various processes are, for example, processes performed by the learning unit 61 and the converter accumulation unit 62.

The learning unit 61 acquires a converter used to acquire a positive bioimage which is a converted bioimage from a negative bioimage by using the one or more negative bioimages and one or more converted bioimages of the bioimage storage unit 11. Since such a learning process is a known technique in the art, a detailed description thereof is omitted. The learning unit 61 usually acquires the converter by a machine learning algorithm. The machine learning algorithm is, for example, deep learning, but it is not particularly limited.

The converter storage unit 62 accumulates the converter acquired by the learning unit 61. The converter accumulation unit 62 accumulates the converter in the storage unit 5, for example.

The storage unit 5 and the bioimage storage unit 11 may suitably use non-volatile recording media, but volatile recording media can also be used.

The process of storing information in the storage unit 5 or the like is not particularly limited. Information may for example be stored in the storage unit 5 or the like via a recording medium, or information transmitted via a communication line or the like may be stored in the storage unit 5 or the like. Alternatively, information input via an input device may be stored in the storage unit 5 or the like.

The processing unit 6, the learning unit 61, and the converter accumulation unit 62 can usually be implemented by an MPU, a memory, or the like. The processing procedure of the processing unit 6 and the like is usually implemented by software, and the software is recorded on a recording medium such as a ROM. However, it may be implemented by hardware (a dedicated circuit).

Figure 11:
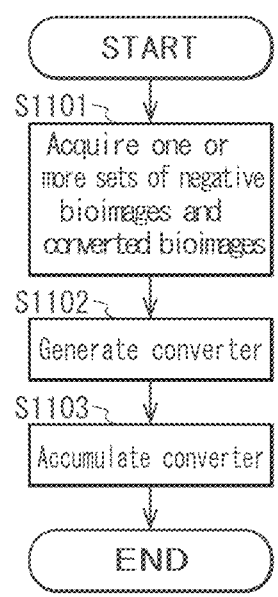
FIG. 11 is a flowchart describing an operation example of the converter generating device B according to a second embodiment.

Next, an operation example of the converter generating device B will be described referring to the flowchart of FIG. 11.

(Step S1101) The learning unit 61 acquires one or more sets of negative bioimages and converted bioimages from the bioimage storage unit 11.

(Step S1102) The learning unit 61 generates a converter having a negative bioimage as input and a converted bioimage as output using the one or more pairs of bioimages acquired in step S1101.

(Step S1103) The converter accumulation unit 62 accumulates the converter generated in step S1102 in the storage unit 5. The routine is then terminated.

As described above, according to this embodiment, a highly precise converter for acquiring a positive bioimage from a negative bioimage can be automatically acquired.

In the present embodiment, the converter generating device B may have part or all of the functions of the bioimage acquiring device A.

The software that implements the converter generating device B in the present embodiment is the program described below. Specifically, the program causes a computer that can access a bioimage storage unit that stores one or more negative bioimages supplied to the bioimage acquiring device A and one or more converted bioimages acquired by the first conversion unit of the bioimage acquiring device A, to function as a learning unit for acquiring a converter used to acquire a positive bioimage, which is a converted bioimage, from a negative bioimage using the one or more negative bioimages and one or more converted bioimages of the bioimage storage unit, and as a converter accumulation unit for accumulating the converter acquired by the learning unit.

Embodiment 3

In this embodiment, a bioimage acquiring device for acquiring a positive bioimage using the converter generated by the converter generating device B will be described.

Figure 12:
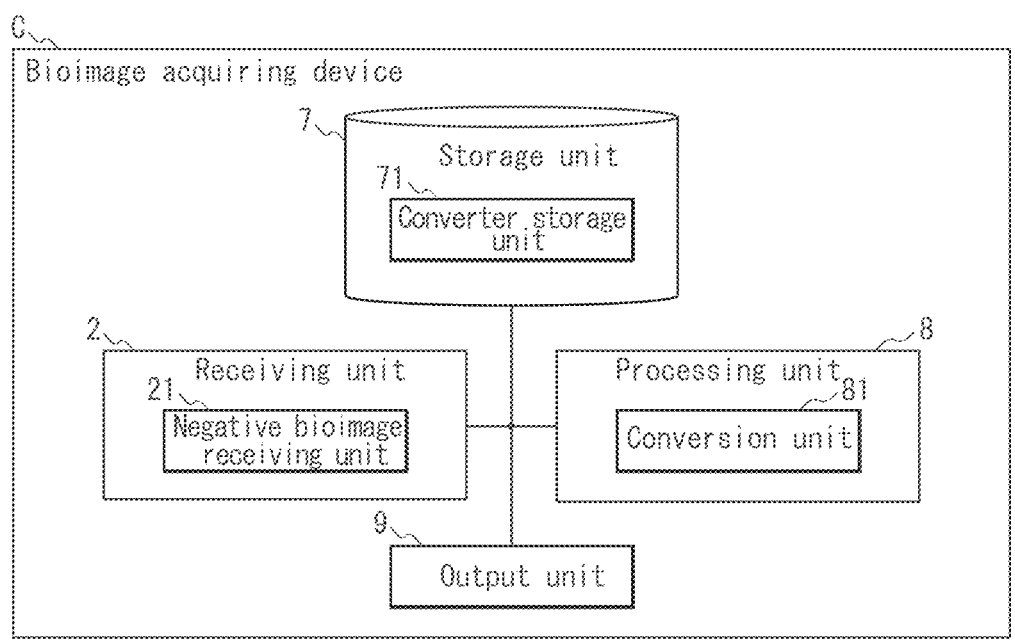
FIG. 12 is a block diagram of a bioimage acquiring device C according to a third embodiment.

FIG. 12 is a block diagram of a bioimage acquiring device C according to the present embodiment. The bioimage acquiring device C comprises a storage unit 7, a receiving unit 2, a processing unit 8, and an output unit 9. The storage unit 7 comprises a converter storage unit 71. The receiving unit 2 comprises a negative bioimage receiving unit 22. The processing unit 8 comprises a conversion unit 81.

Various types of information are stored in the storage unit 7. The various types of information are, for example, a converter and a bioimage.

The converter storage unit 71 stores the converter acquired by the converter generating device B.

The processing unit 8 performs various processes. The various processes are, for example, processes performed by the conversion unit 81. The processing unit 8 may comprise a classifying unit 32.

The conversion unit 81 converts the negative bioimage received by the negative bioimage receiving unit 22 using the converter of the converter storage unit 71, and acquires a positive bioimage which is the conversion result. Since the processing of the conversion unit 81 is a known technique in the art, a detailed description thereof is omitted. The conversion unit 81 may be identical to the first conversion unit 31.

The output unit 9 outputs the positive bioimage acquired by the conversion unit 81. The output unit 9 usually stores positive bioimages acquired by the conversion unit 81. The storage location for positive bioimages is, for example, the storage unit 7, but it is not particularly limited.

The storage unit 7 and the converter storage unit 71 may suitably use non-volatile recording media, but volatile recording media can also be used.

The process of storing information in the storage unit 7 or the like is not particularly limited. Information may for example be stored in the storage unit 7 or the like via a recording medium, or information transmitted via a communication line or the like may be stored in the storage unit 7 or the like. Alternatively, information input via an input device may be stored in the storage unit 7 or the like.

The processing unit 8, the conversion unit 81, and the output unit 9 are usually implemented by an MPU, a memory, or the like. The processing procedure of the processing unit 8 and the like is usually implemented by software, and the software is recorded on a recording medium such as a ROM. However, it may be implemented by hardware (a dedicated circuit).

Next, an operation example of the bioimage acquiring device C will be described referring to the flowchart of FIG. 13.

(Step S1301) It is determined whether or not the negative bioimage receiving unit 22 has received a negative bioimage. If a negative bioimage has been received, the routine proceeds to step S1302, and if a negative bioimage has not been received, the routine returns to step S1301.

(Step S1302) The conversion unit 81 acquires a converter from the converter storage unit 71.

(Step S1303) The conversion unit 81 converts the negative bioimage received in step S1301 using the converter acquired in step S1302, and acquires the positive bioimage which is the conversion result.

(Step S1304) The output unit 9 stores the positive bioimages acquired in step S1303. The routine returns to step S1301.

Figure 13:
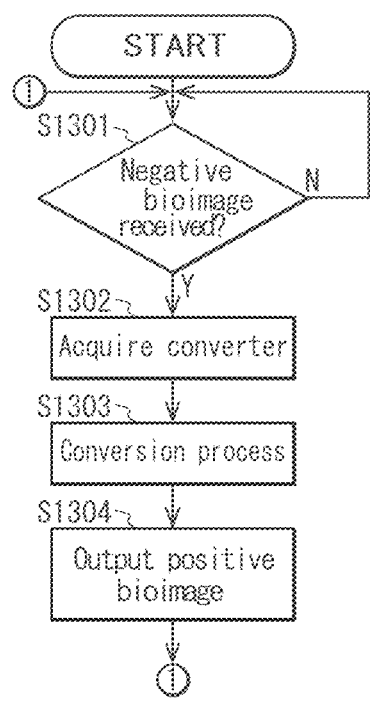
FIG. 13 is a flowchart illustrating an operation example of the bioimage acquiring device C according to a third embodiment.

Note that in the flowchart of FIG. 13, when the power is turned off or a process terminate interrupt is issued, the process terminates.

As described above, according to the present embodiment, a positive bioimage can be acquired from a negative bioimage using an automatically acquired, highly precise converter.

The software that implements the bioimage acquiring device C in the present embodiment is the program described below. Specifically, the program causes a computer that can access the converter storage unit that stores the converter acquired by the converter generating device B, to function as a conversion unit that converts a negative bioimage received by the negative bioimage receiving unit using the converter stored in the converter storage unit, and acquires a positive bioimage which is the conversion result, and as an output unit that outputs the positive bioimage acquired by the conversion unit.

Figure 14:
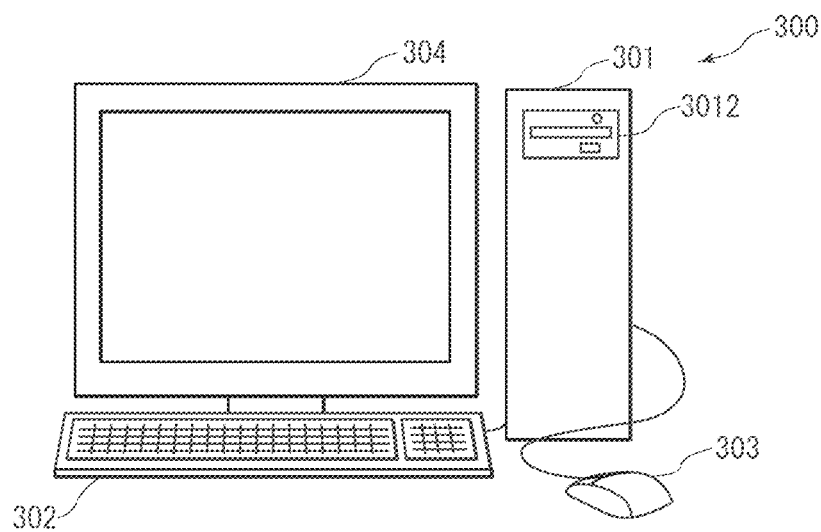
FIG. 14 is a schematic diagram of a computer system according to the above embodiment.

FIG. 14 shows the external appearance of a computer that executes the programs described in the present specification to implement the various embodiments described above (for example, the bioimage acquiring device A). The above embodiments can be implemented by computer hardware, and by computer programs running on it. FIG. 14 is a schematic view of a computer system 300, and FIG. 15 is a block diagram of the system 300.

In FIG. 14, the computer system 300 comprises a computer 301 having a CD-ROM drive, a keyboard 302, a mouse 303, and a monitor 304.

Figure 15:
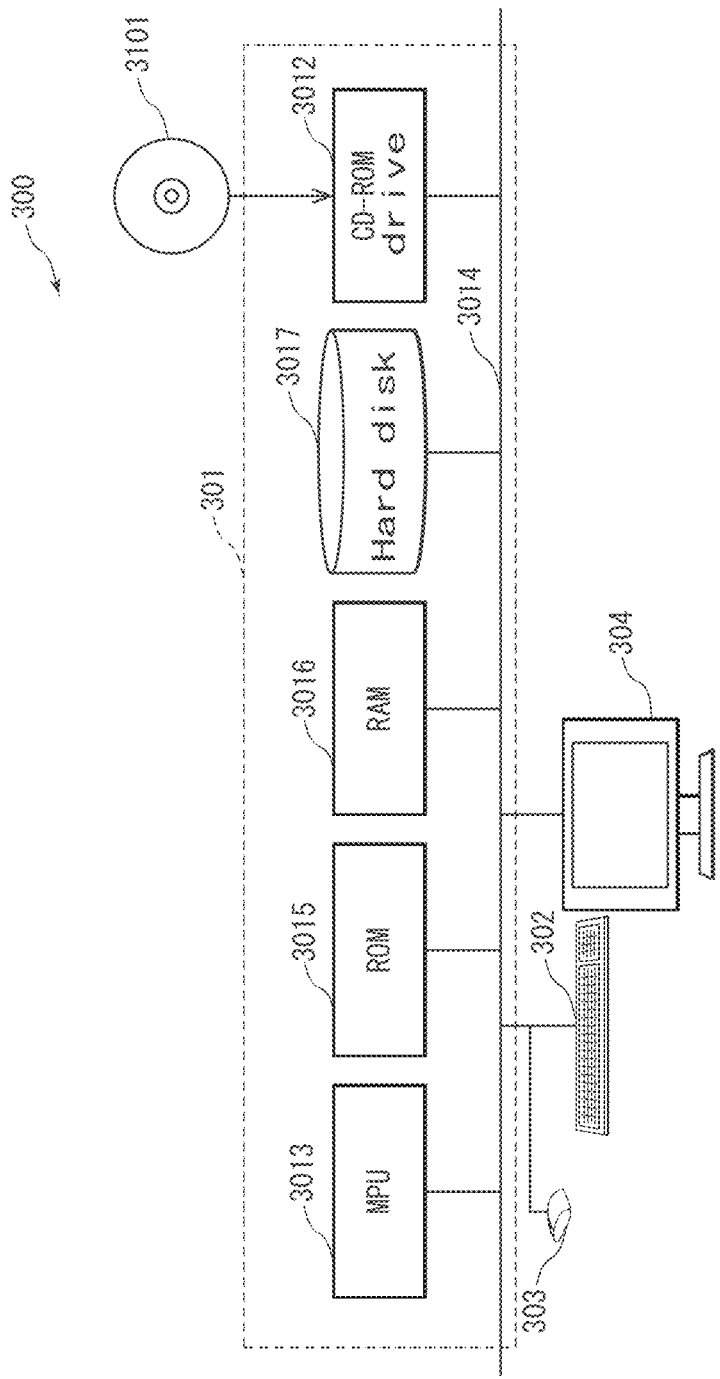
FIG. 15 is a block diagram of the computer system according to the above embodiment.

In FIG. 15, the computer 301, in addition to a CD-ROM drive 3012, comprises an MPU 3013, a bus 3014 connected to the MPU 3013 and the CD-ROM drive 3012, a ROM 3015 for storing a program such as a boot-up program, a RAM 3016 connected to the MPU 3013 for temporarily storing instructions of an application program and providing temporary storage space, and a hard disk 3017 for storing the application program, the system program, and data. Although not shown here, the computer 301 may further comprise a network card that provides a connection to a LAN.

A program for causing the computer system 300 to execute the functions of the bioimage acquiring device A and the like according to the above-described embodiments may be stored in the CD-ROM 3101, inserted into the CD-ROM drive 3012, and further transferred to the hard disk 3017. Alternatively, the program may be transmitted to the computer 301 via a network, not shown, and stored on the hard disk 3017. The program is loaded into the RAM 3016 at runtime. The program may be loaded directly from the CD-ROM 3101 or a network.

The program does not necessarily comprise an operating system (OS) that causes the computer 301 to execute the functions of the bioimage acquiring device A or the like according to the above-described embodiments, or a third-party program or the like. The program needs only comprise part of the instructions that call the appropriate functions (modules) in a controlled manner to obtain the desired result. It is well known how the computer system 300 works, and a detailed description thereof is omitted.

In the above program, in the step of transmitting information and the step of receiving information, processing performed by hardware, for example, processing performed by a modem or interface card in the transmission step (processing performed only by hardware), is not included.

The number of computers that execute the above program may be singular or plural. Specifically, centralized processing may be performed, or distributed processing may be performed.

In each of the above embodiments, the above program may be singular or plural. Specifically, as a known technique for processing by AI, a process (ensemble process) may be performed wherein a plurality of AIs are trained simultaneously, and the average value or linear combination sum of the determination results is adopted as the final result.

In each of the above embodiments, it will be understood that two or more communication means existing in one device may be physically implemented by one medium.

It will be understood that the present invention is not particularly limited to the above embodiments, various modifications being possible which are also comprised within the scope of the present invention.

INDUSTRIAL APPLICABILITY

As described above, the bioimage acquiring device according to the present invention has the advantageous effect of being able to precisely acquire a positive bioimage with few defects from a negative bioimage having defects such as metal artifacts, and is useful as a bioimage acquiring device or the like.

What is claimed:
1. A bioimage acquiring device, comprising:
a classifier storage unit that stores a classifier that determines whether a bioimage is a negative bioimage or a positive bioimage;
wherein the classifier is created by using one or more negative bioimages which are defective bioimages and one or more positive bioimages which are non-defective bioimages;
a converter storage unit that stores a first converter used for a conversion process to acquire a positive bioimage from a negative bioimage;
a negative bioimage receiving unit that receives negative bioimages;
a first conversion unit that performs a first conversion process of converting a negative bioimage received by the negative bioimage receiving unit using the first converter, and acquiring a converted bioimage which is the conversion result; and a classifying unit that performs a first classifying process for determining whether the converted bioimage acquired by the first conversion unit is a positive bioimage or a negative bioimage, wherein:

the first conversion unit performs a learning process using the determination result of the classifying unit and the converted bioimage, and performs an update process for updating the first converter, the negative bioimage receiving unit receives a new negative bioimage, and the first conversion unit converts the new negative bioimage received by the negative bioimage receiving unit using the updated first converter, and acquires a converted bioimage which is the conversion result.

2. The bioimage acquiring device according to claim 1, further comprising:

a bioimage storage unit that stores the one or more negative bioimages and the one or more positive bioimages; and a learning unit that generates a classifier used for determining whether the received bioimage is a positive bioimage or a negative bioimage using, in addition to one or more negative bioimages and one or more positive bioimages of the bioimage storage unit, one or more converted bioimages acquired by the first conversion unit as negative bioimages.

3. The bioimage acquiring device according to claim 1, further comprising:

a feature amount vector acquiring unit that acquires an input feature amount vector which is one or more features of the negative bioimage supplied to the first conversion unit and an output feature amount vector which is one or more features of the converted bioimage acquired by the first conversion unit; and a feature amount difference information acquiring unit that acquires feature amount difference information relating to the difference between the input feature amount vector and the output feature amount vector, wherein:

the first conversion unit performs a learning process so that the feature amount difference information is reduced, and updates the first converter.

4. The bioimage acquiring device according to claim 1, wherein:

the converter storage unit stores a second converter used for a conversion process for acquiring a negative bioimage from a positive bioimage, further comprises a second conversion unit that converts the converted bioimage acquired by the first conversion unit using the second converter, and performs a second conversion process to acquire a second converted bioimage which is the conversion result, the first conversion unit converts the second converted bioimage acquired by the second conversion unit using the first converter, the classifying unit performs a second classifying process for determining whether the converted bioimage acquired by the first conversion unit from the second converted bioimage is a positive bioimage or a negative bioimage, and further comprises a control unit that performs control such that the first conversion process, the first classifying process, the second conversion process, and the second classifying process are performed once, twice or more times.

5. The bioimage acquiring device according to claim 4, further comprising:

a feature amount vector acquiring unit that acquires a feature amount vector of at least two of a converted bioimage which is an input to the second conversion unit, a second converted bioimage which is an output of the second conversion unit, and a converted bioimage which is an output for the second converted bioimage from the first conversion unit; and a feature amount difference information acquiring unit that acquires feature amount difference information relating to the difference between at least one pair of two or more feature amount vectors which are acquired by the feature amount vector acquiring unit, wherein:

the first conversion unit performs the learning process so that the feature amount difference information is reduced, and updates the first converter.

6. The bioimage acquiring device according to claim 1, wherein:

the negative bioimage is a set of two or more slice images obtained by cutting a part of a defective image set of an imaged living body into round slices, and the positive bioimage is a set of two or more slice images obtained by cutting a part of a non-defective image set of the imaged living body into round slices.

7. The bioimage acquiring device according to claim 1, wherein:

the first conversion unit performs the first conversion process only for pixels having a pixel value in a predetermined range, and the classifying unit performs a first classifying process for determining whether the image that is acquired by the first conversion unit is a positive bioimage or a negative bioimage, using a classifier created for only pixels having a pixel value in the predetermined range.

8. The bioimage acquiring device according to claim 7, wherein the pixels having a pixel value in the predetermined range are pixels constituting a bone image.

9. The bioimage acquiring device according to claim 1, further comprising a bioimage receiving unit that receives two or more bioimages, wherein:

the classifying unit determines whether each of the two or more bioimages received by the bioimage receiving unit is a positive bioimage or a negative bioimage using the classifier; and the negative bioimage receiving unit acquires a bioimage determined by the classifying unit to be a negative bioimage.

10. A converter generating device, comprising:

a bioimage storage unit that stores the one or more negative bioimages supplied to the bioimage acquiring device according to claim 1, and the one or more converted bioimages acquired by the first conversion unit of the bioimage acquiring device according to claim 1;

a learning unit that acquires a converter used to obtain a positive bioimage, which is a converted bioimage, from a negative bioimage using the one or more negative bioimages and the one or more converted bioimages of the bioimage storage unit; and a converter accumulation unit that stores the converter acquired by the learning unit.

11. A bioimage generating method, implemented by a classifier storage unit that stores a classifier that determines whether a bioimage is a negative bioimage or a positive bioimage, wherein the classifier is created by using one or more negative bioimages which are defective bioimages and one or more positive bioimages which are non-defective bioimages, and a converter storage unit that stores a first converter used for a conversion process to acquire a positive bioimage from a negative bioimage, a negative bioimage receiving unit, a first conversion unit, and a classifying unit, said method comprising:
- a negative bioimage receiving step wherein the negative bioimage receiving unit receives a negative bioimage;
- a first conversion step wherein the first conversion unit performs a first conversion process of converting a negative bioimage received in the negative bioimage receiving step using the first converter and acquiring a converted bioimage which is the conversion result;
- a classifying step, wherein the classifying unit performs a first classifying process for determining whether the converted bioimage acquired by the first conversion unit is a positive bioimage or a negative bioimage using the classifier;
- an updating step, wherein the first conversion unit performs a learning process using the determination result and the converted bioimage in the classification step, and updates the first converter;
- a second negative bioimage receiving step, wherein the negative bioimage receiving unit receives a new negative bioimage; and
- a converted bioimage using the updated first converter, and acquires the converted bioimage which is the conversion result.

12. A converter generating method implemented by a bioimage storage unit that stores the one or more negative bioimages supplied to the bioimage acquiring device according to claim 1, and the one or more converted bioimages acquired by the first conversion unit of the bioimage acquiring device according to claim 1, a learning unit, and a converter accumulation unit, said method comprising:
- a learning step wherein the learning unit acquires a converter used for acquiring a positive bioimage which is a converted bioimage from the negative bioimage by using the one or more negative bioimages and the one or more converted bioimages of the bioimage storage unit; and
- a converter accumulation step wherein the converter accumulation unit stores the converter acquired by the learning unit.

13. A non-transitory recording medium on which a program is recorded for causing a computer that can access a classifier storage unit that stores a classifier created by using one or more negative bioimages that are defective bioimages and one or more positive bioimages that are non-defective bioimages to determine whether the image is a negative bioimage or a positive bioimage, and a converter storage unit that stores a first converter used for a conversion process that attempts to acquire a positive bioimage from a negative bioimage, to function as:
- a negative bioimage receiving unit that receives a negative bioimage;
- a first conversion unit that converts a negative bioimage received by the negative bioimage receiving unit using the first converter, and performs a first conversion process that acquires the converted bioimage which is the conversion result; and
- a classifying unit that performs a first classifying process for determining whether the converted bioimage acquired by the first conversion unit is a positive bioimage or a negative bioimage using the classifier, wherein:
- the first conversion unit performs a learning process using the determination result of the classifying unit and the converted bioimage, and an update process that updates the first converter,
- the negative bioimage receiving unit receives a new negative bioimage, and
- the first conversion unit converts the new negative bioimage received by the negative bioimage receiving unit using the updated first converter, and acquires the converted bioimage which is the conversion result.

14. A non-transitory recording medium on which a program is recorded for causing a computer that can access a bioimage storage unit in which the one or more negative bioimages supplied to the bioimage acquiring device according to claim 1, and the one or more converted bioimages acquired by the first conversion unit of the bioimage acquiring device according to claim 1 are stored, to function as:
- a learning unit that acquires a converter used for acquiring a positive bioimage which is a converted bioimage from a negative bioimage using the one or more negative bioimages and the one or more converted bioimages of the bioimage storage unit; and
- a converter accumulation unit that accumulates the converter acquired by the learning unit.

* * * * *